United States Patent [19]

Lawrence

[11] Patent Number: 4,931,441

[45] Date of Patent: Jun. 5, 1990

[54] STABILIZED AQUEOUS LEUCOVORIN CALCIUM COMPOSITIONS

[75] Inventor: Richard P. Lawrence, Sayville, N.Y.

[73] Assignee: Luitpold Pharmaceuticals, Inc., Shirley, N.Y.

[21] Appl. No.: 269,130

[22] Filed: Nov. 9, 1988

[51] Int. Cl.$^5$ .................... A61K 31/50; A61K 31/495
[52] U.S. Cl. .................................................. 514/249
[58] Field of Search ......................................... 514/249

[56] References Cited

U.S. PATENT DOCUMENTS 4,350,659 9/1982 Riceberg ............................ 544/261

Primary Examiner—Douglas W. Robinson
Assistant Examiner—Raymond J. Henley, III
Attorney, Agent, or Firm—Cooper & Dunham

[57] ABSTRACT

A leucovorin composition having improved properties is provided by an aqueous, isotonic, sterile leucovorin calcium solution having a pH in the range 6.5–8.5 and containing as a buffer therein sodium citrate dihydrate in the amount in the range 1 mg–32 mg/mL, the leucovorin composition containing leucovorin calcium pentahydrate in the amount 6.35 mg/mL, equivalent to 5 mg/mL leucovorin content. A preferred sterile, aqueous leucovorin solution in accordance with this invention contains 6.35 mg/mL leucovorin calcium pentahydrate, 22 mg/mL sodium citrate dihydrate, the remainder being sterile water. The pH of this solution is adjusted to 8.1±0.1 with 1N NaOH solution and/or 1N citric acid solution.

13 Claims, No Drawings

STABILIZED AQUEOUS LEUCOVORIN CALCIUM COMPOSITIONS

BACKGROUND OF THE INVENTION

Leucovorin is a mixture of diastereoeisomers of the 5-formyl derivative of tetrahydrofolic acid. The biologically active compound of the mixture is the (−)-L-isomer, known as Citrovorum factor or (−)-folinic acid. Leucovorin is a water-soluble vitamin in the folate group and is useful as an antidote to drugs which act as folic acid antagonists. Leucovorin is employed in injection form as leucovorin calcium in an aqueous bacteriostatic preparation containing leucovorin present as the calcium salt pentahydrate of N-[4-[[(2-amino-5-formyl-1,4,5,6,7,8-hexahydro-4-oxo-6-pteri-dinyl)-methyl-amino- b enzoyl]-L-glutamic acid. Each 5 mg of leucovorin is equivalent to 5.4 mg of anhydrous leucovorin calcium or 6.35 mg of leucovorin calcium pentahydrate.

The administration of leucovorin calcium, such as by injection, is indicated (a) to diminish the toxicity of and to counteract the effect of inadvertently administered dosages of folic acid antagonists and (b) in the treatment of megaloblastic anemias due to sprue, nutritional deficiency, pregnancy and infancy when oral therapy is not feasible. In the treatment of an accidental overdosage of folic acid antagonist leucovorin should be administered as promptly as possible as the time interval between anti-folate administration, e.g. methotrexate, and leucovorin rescue increases the effectiveness of leucovorin in counteracting hematologic toxocity diminishes. Monitoring of serum methotrexate concentration is essential in determining the optimal dose of duration and treatment with leucovorin so that the resulting levels of tetrahydrofolate are equivalent to or greater than that of methotrexate.

Leucovorin calcium is susceptible to hydrolysis. The rate of degradation due to hydrolysis increases as the pH drops below 7. Because of the desirability of matching the amount of leucovorin administered as an antidote to at least match the folic acid antagonist drugs administered, such as in the treatment of acute leukemia, or to counteract an overdose in the administration of an anti-folate, such as methotrexate, to effect leucovorin rescue and since leucovorin rescue must be administered as promptly as possible, it is desirable to make certain that the leucovorin composition administered is of the desired and/or required strength as indicated on the container of the drug. Since leucovorin undergoes hydrolysis at a pH below 7.0, such as in the range 6.5–7.0, it is therefore desirable to have available and employ a leucovorin composition which is stable and retains its original packaged potency, pH and clarity.

It is an object of this invention to provide a leucovorin composition, such as an aqueous leucovorin calcium aqueous composition, which has improved stability.

It is another object of this invention to provide a method of improving the stability of an aqueous leucovorin composition, such as an aqueous leucovorin calcium composition, wherein leucovorin calcium is dissolved in sterile or bacteriostatic water.

It is yet another object of this invention to provide an aqueous leucovorin composition suitable for injection wherein the leucovorin composition in form for injection use is packaged or treated so as to retain as much as possible and for a relatively long time its original potency, pH and clarity, and having improved stability.

How these and other objects of this invention are achieved will become apparent from the accompanying disclosure. In at least one embodiment of the practices of this invention at least one of the foregoing objects will be achieved.

SUMMARY OF THE INVENTION

Aqueous leucovorin compositions, particularly leucovorin compositions suitable for injection use, such as a leucovorin calcium pentahydrate solution in sterile water, have improved stability, e.g. potency, pH maintenance and clarity, when there is provided in such compositions a buffer, such as sodium citrate, particularly sodium citrate dihydrate. When leucovorin compositions, particularly leucovorin calcium compositions, in accordance with this invention are prepared, such compositions are prepared and the pH adjusted to a value in the range not less than 6.5 and not higher than 8.5. The pH of the composition is initially adjusted to the desired pH by the addition thereto of NaOH and/or citric acid, such as 1N NaOH and/or 1N citric acid. It is also desirable that the resulting produced leucovorin product for injection purposes prepared in accordance with this invention be isotonic. Therefore, in the preparation of such solutions, the amount of added buffering agent, e.g. sodium citrate, should be controlled so as not to be present in the resulting composition in an amount greater than 32 mg/mL sodium citrate since above that concentration the resulting leucovorin composition will no longer be isotonic.

As indicated hereinabove, it is desirable in the makeup of leucovorin compositions in accordance with this invention that a suitable amount of buffering agent sodium citrate be employed. At a minimum the amount of sodium citrate present in the leucovorin composition in accordance with this invention should not be less than 1 mg/mL, at which concentration the citrate will begin to buffer. Since relatively rapid degradation of leucovorin, such as leucovorin calcium, occurs at a pH in the range 6.5–7.0, to prevent degradation at this pH range the leucovorin composition is buffered with sodium citrate dihydrate at a pH of 8.1±0.1 . Usefully, the sodium citrate also acts as a chelating agent further improving the stability and properties of leucovorin compositions containing the and at the concentration indicated the sodium citrate helps make the leucovorin composition or solution isotonic.

DETAILED DESCRIPTION OF THE INVENTION

Leucovorin calcium compositions suitable for injection, such as leucovorin calcium aqueous compositions or solutions containing 5 mg/mL leucovorin, are desirably buffered with sodium citrate dihydrate in accordance with this invention at or to a pH of 8.1. Such leucovorin for each mL thereof would contain 6.35 mg leucovorin calcium pentahydrate equivalent to 5 mg/mL leucovorin content, 22.0 mg sodium citrate dihydrate, the remaining being made up of water, preferably sterile water, and the pH desirably adjusted to a value in the range 8.1±0.1 with 1N NaOH and/or 1N citric acid. When this leucovorin calcium composition suitable for injection use is so prepared and buffered with sodium citrate, the resulting product has improved stability, e.g. potency, pH and clarity and, moreover, the resulting product exhibits improved properties over other conventional available leucovorin compositions for similar uses.

Although it is preferred to prepare leucovorin calcium compositions in accordance with this invention at a pH adjusted to 8.1±0.1, leucovorin calcium compositions are also usefully prepared having a pH in the range 6.5–8.5 with citric acid added at a concentration of 1 mg/mL to 32 mg/mL. The following is the make-up of 1 mL of a leucovorin composition in accordance with this invention.

| | |
|---|---|
| Leucovorin Calcium Pentahydrate (Equivalent to 5 mg/mL Leucovorin Content) | 6.35 mg |
| Sodium Citrate (Dihydrate) | 22.0 mg |
| Water for Injection | q.s. | pH adjusted to 8.1±0.1 with 1N NaOH and/or 1N citric acid.

Desirably, leucovorin compositions in accordance with this invention are packaged in an airtight, sealed container or ampule in measured amounts, such as 1 mL quantities or higher multiples thereof, e.g. 5 mL. Providing such compositions in a sealed ampule or container makes administration of the composition in dosage units readily available and permits ease of administration. Also, when properly packaged so as to be airtight and sealed, the requirement or necessity for incorporating a preservative, such as benzyl alcohol, in the packaged leucovorin composition is reduced.

As will be apparent to those skilled in the light of the foregoing disclosures, many modifications, alterations and substitutions are possible int he practice of this invention without departing from the spirit or scope thereof.

I claim:

1. A leucovorin calcium composition comprising an aqueous solution of leucovorin calcium pentahydrate in the amount of about 6.35 mg per mL of solution, said solution being adjusted to a pH in the range 6.5–8.5 by the addition of sodium hydroxide and/or citric acid and 14 comprising sodium citrate or sodium citrate dihydrate as a stabilizing and buffering agent.

2. A composition in accordance with claim 1 wherein the pH is adjusted with an effective amount of 1 N NaOH and/or 1N citric acid to about 8.1.

3. A composition in accordance with claim 1 wherein said solution is rendered isotonic by the addition of sodium citrate dihydrate to a concentration in the range 22–32 mg/mL.

4. A composition in accordance with claim 1 wherein each mL of said solution is buffered with sodium citrate dihydrate and/or sodium citrate in an amount in the range 1–32 mg.

5. A composition in accordance with claim 4 wherein the pH of the solution is in the range 6.5–8.5.

6. A composition in accordance with claim 1 wherein 1 mL of said solution contains 6.35 mg leucovorin calcium pentahydrate equivalent to 5 mg leucovorin, 22.0 mg sodium citrate dihydrate, said solution having a pH of 8.1 ±0.1 adjusted with an effective amount 1N NaOH aqueous solution and/or 1N aqueous citric acid solution.

7. A sealed, airtight ampule or container containing a leucovorin calcium composition in accordance with claim 1.

8. An ampule or container in accordance with claim 7 wherein 1 mL of said leucovorin calcium composition therein provides 5 mg/mL leucovorin.

9. A sealed, airtight ampule or container containing the leucovorin calcium pentahydrate solution in accordance with claim 6.

10. A sealed, airtight ampule or container wherein said ampule contains a leucovorin calcium solution in accordance with claim 1 and wherein said leucovorin calcium solution contains 22.0 mg sodium citrate dihydrate and has a pH of 8.1±0.1 adjusted with an effective amount of a 1 N NaOH aqueous solution and/or aqueous citric acid solution.

11. A method of improving the stability of a sterile isotonic aqueous leucovorin calcium solution by incorporating sodium citrate in said solution in an amount in the range 1 mg–32 mg per mL of said solution, said solution having a pH in the range 6.5–8.5.

12. A method in accordance with claim 11 wherein the pH of said solution is adjusted by adding an effective amount of NaOH and/or citric acid.

13. A method in accordance with claim 12 wherein the added NaOH is 1N NaOH aqueous solution and the added citric acid is 1N citric acid aqueous solution.

* * * * *